(12) United States Patent
Kessler et al.

(10) Patent No.: US 6,872,702 B1
(45) Date of Patent: Mar. 29, 2005

(54) INHIBITORS FOR UROKINASE RECEPTOR

(75) Inventors: Horst Kessler, Schwalbach-Limes (DE); Heinrich Graeff, München (DE); Manfred Schmitt, München (DE); Viktor Magdolen, Kirchheim (DE); Olaf G. Wilhelm, München (DE); Christoph Riemer, München (DE); Markus Bürgle, München (DE)

(73) Assignee: Wilex AG, Munich (DE)

( * ) Notice: Subject to any disclaimer, the term of this patent is extended or adjusted under 35 U.S.C. 154(b) by 0 days.

(21) Appl. No.: 09/402,464

(22) PCT Filed: Apr. 14, 1999

(86) PCT No.: PCT/EP98/02179

§ 371 (c)(1),
(2), (4) Date: Jan. 7, 2000

(87) PCT Pub. No.: WO98/46632

PCT Pub. Date: Oct. 22, 1998

(30) Foreign Application Priority Data

Apr. 11, 1997 (EP) ............................................. 97106024

(51) Int. Cl.[7] .............................................. A61K 38/12
(52) U.S. Cl. .......................... 514/11; 514/15; 530/317; 530/323; 530/333; 530/344
(58) Field of Search ..................... 514/11, 15; 530/317, 530/323, 333, 344

(56) References Cited

FOREIGN PATENT DOCUMENTS

| WO | WO 94/22464 | * 10/1994 |
| WO | 94 22464 | 10/1994 |
| WO | 95 14714 | 6/1995 |

OTHER PUBLICATIONS

V. Magdolen et al., "Systematic mutational analysis of the receptor–binding region of the human urokinase–type plasminogen activator", Eur. J. Biochem., vol. 237, 1996, pp. 237–251.

I. M. Takenaka et al., "Hsc70–binding Peptides Selected from a Phage Display Peptide Library that Resemble Organellar Targetting Sequences", J. Biol. Chem, vol. 270, No. 34, 1995, pp. 19839–19844.

Kini et al. "A Common Structural Feature Enclosing Interaction Sites: Prediction of Protein—Protein Interaction Sites and Development of Potent Bioactive Peptides" Current Topics in Peptides and Protein Res., I (1994) pp 297–311.*

* cited by examiner

Primary Examiner—Brenda Brumback
Assistant Examiner—Anish Gupta
(74) Attorney, Agent, or Firm—Rothwell Figg Ernst & Manbeck

(57) ABSTRACT

The present invention concerns peptides as inhibitors of the binding of urokinase to the urokinase receptor. These peptides, which are preferably cyclic, are suitable as pharmaceutical agents for diseases that are mediated by urokinase and its receptor.

26 Claims, 5 Drawing Sheets native uPAR binding domain of uPA
Seq. ID No: 2 peptide
cyclo$^{19,31}$ uPA$_{19-31}$
Seq. ID No: 3

Seq. ID No: 4

SEQUENCE LISTING

<160> NUMBER OF SEQ ID NOS: 4

<210> SEQ ID NO 1
<211> LENGTH: 17
<212> TYPE: PRT
<213> ORGANISM: Homo sapiens

<400> SEQUENCE: 1

Ala Glu Pro Met Pro His Ser Leu Asn Phe Ser Gln Tyr Leu Trp Tyr
 1               5                  10                  15

Thr

<210> SEQ ID NO 2
<211> LENGTH: 15
<212> TYPE: PRT
<213> ORGANISM: Homo sapiens

<400> SEQUENCE: 2

```
                        -continued

Thr Cys Val Ser Asn Lys Tyr Phe Ser Asn Ile His Trp Cys Asn
 1           5               10               15

<210> SEQ ID NO 3
<211> LENGTH: 13
<212> TYPE: PRT
<213> ORGANISM: Homo sapiens
<220> FEATURE:
<221> NAME/KEY: Domain
<222> LOCATION: 1...12
<223> OTHER INFORMATION: D-amino acids may be substituted for
      corresponding L-amino acids at positions 1,2,3,9, 11, and 12.

<400> SEQUENCE: 3

Cys Val Ser Asn Lys Tyr Phe Ser Asn Ile His Trp Cys
 1           5               10

<210> SEQ ID NO 4
<211> LENGTH: 10
<212> TYPE: PRT
<213> ORGANISM: Homo sapiens

<400> SEQUENCE: 4

Cys Asn Lys Tyr Phe Ser Asn Ile Cys Trp
 1           5               10
```

INHIBITORS FOR UROKINASE RECEPTOR

This application is a national stage entry of International Application No. PCT/EP98/02179, filed Apr. 14, 1998 designating the U.S., which claims the benefit of European Application No. 97 106 024.9, filed Apr. 11, 1997.

The present invention concerns peptides as inhibitors of the binding of urokinase to the urokinase receptor. These peptides which are preferably cyclic are suitable as pharmaceutical agents for diseases which are mediated by urokinase and its receptor.

The serine protease uPA (urokinase-type plasminogen activator) is responsible for various physiological and pathological processes such as the proteolytic degradation of extracellular matrix material which is necessary for the invasiveness and migration of cells and for tissue remodelling. uPA binds with high affinity ($K_D=10^{-10}-10^{-9}$ M) to the membrane-based uPA receptor (uPAR) on the cell surface.

The binding of uPA to its receptor is involved in many invasive biological processes such as the metastatic spread of malignant tumours, trophoplast implantation, inflammation and angiogenesis. Hence antagonists of uPA are able to inhibit the invasiveness, metastatic spread and angiogenesis of tumours. uPA antagonists can be used as agents for the treatment of invasive and metastasising cancer diseases in which uPA and uPAR occur at the invasive foci of tumours (Dano et al., The receptor for urokinase plasminogen activator: Stromal cell involvement in extracellular proteolysis during cancer invasion, in: Proteolysis and Protein Turnover, Barrett, A. J. and Bond, J., Editor, Portland Press, London, 1994, 239) e.g. in cancers of the breast, lung, intestine and ovaries. In addition uPA antagonists can also be used for other purposes in which it is necessary to inhibit the proteolytic activation of plasminogen, for example to treat diseases such as arthritis, inflammation, osteoporosis, retinopathies and for contraception.

The uPA receptor is described in WO 90/12091 and in the publications by Ploug et al., J. Biol. Chem. 268 (1993), 17539 and Ronne et al., J. Immunol. Methods 167 (1994), 91.

uPA is synthesized as a single chain molecule (pro-uPA) and is converted enzymatically into an active two-chain uPA. The uPA molecule is composed of three structurally independent domains, the N-terminal growth factor-like domain (GFD, uPA 1–46), a kringle structure domain (uPA 45–135) and the serine protease domain (uPA 159–411). GFD and the kringle domain together form the so-called aminoterminal fragment of uPA (ATF, uPA 1–135) which is produced by further proteolytic cleavage of two-chain uPA. ATF binds to the uPA receptor with a similar affinity as uPA.

The receptor-binding region of uPA spans the region of the amino acids 12 to 32 since a peptide which contains the amino acid residues 12 to 32 of uPA (in which case cysteine is replaced by alanine in position 19) competes with ATF for binding to the uPA receptor (Appella et al., J. Biol. Chem. 262 (1987), 4437–4440). In this publication it was also shown that this peptide also has an affinity for the uPA receptor after cyclization by bridging the two cysteine residues at positions 12 and 32. In an alternative approach Goodson et al., (Proc. Natl. Acad. USA 91 (1994), 7129–7133) identified antagonistic uPA peptides for the uPAR by screening a bacteriophage peptide library. These peptides had no apparent sequence homology to the natural uPAR-binding sequence of uPA.

Further investigations of the uPAR-binding region of uPA are described in recent publications (Rettenberger et al., Biol. Chem. Hoppe-Seyler 376 (1995), 587–594); Magdolen et al., Eur. J. Biochem. 237 (1996), 743–751; Goretzki et al., Fibrinolysis and Proteolysis 11 (1997), 11–19). The residues Cys19, Lys23, Tyr24, Phe25, Ile28, Trp30 and Cys31 were identified as important determinants for a uPA/uPAR interaction. In these investigations a uPA peptide having the amino acids 16 to 32 of uPA was identified as the most effective inhibitor.

Magdolen et al., (1996) supra analysed the uPAR binding region of the uPA molecule using a peptide having the amino acids 14 to 32 of uPA and peptides derived therefrom. However, these peptides and also peptides used by other research groups (cf. e.g. Appella et al., (1987) supra) have a relatively low affinity for uPAR.

WO-A-94/22646 discloses linear peptides with a length of 6 to 18 amino acids which are derived from the region of the amino acids 14 to 33 of uPA. It is described that short peptides derived from uPA (uPA 21–29 and uPA 21–26) are able to influence the growth of keratinocytes. Although WO-A-94/22646 makes reference to a potential use of the claimed peptides to block the uPA/uPAR interaction, no data or information whatsoever are shown on such binding studies. Moreover, the peptides uPA 21–29 and uPA 21–26 which are said to be preferred linear peptides do not contain the minimal uPAR binding region of linear uPA peptides which comprises the sequence region of amino acids 19 to 31. Hence the influence of the growth of keratinocytes by these short peptides is very probably not due to a uPA/uPAR interaction.

However, a disadvantage of the previously known uPA peptide inhibitors is that their affinity of binding to the uPA receptor is relatively low and inadequate for a therapeutic application. Thus there is a great need for new uPA peptide antagonists which have a higher affinity for the receptor.

In quantitative investigations it was surprisingly found that the linear peptide uPA (19–31) (SEQ ID NO: 3), cyclic derivatives of this peptide and sequence-modified peptides from this uPA region have a considerably improved affinity of binding to the uPA receptor.

Experimental data demonstrate that the peptides according to the invention can be used as uPA antagonists which bind with high affinity to the uPAR. Cyclic peptides are particularly preferred which are characterized by bridges, especially disulfide bridges, which do not occur in the native uPA molecule.

Hence the present invention concerns peptides having the general structural formula (I):

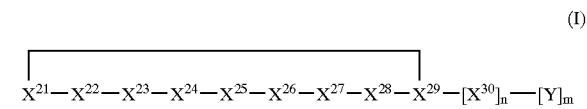

(I)

in which $X^{21}$ to $X^{30}$ each denotes an aminocarboxylic acid, preferably an α-aminocarboxylic acid and $X^{21}$ and $X^{29}$ are bridged together, Y is a spacer m and n are each independently 0 or 1, and the monomeric building blocks are linked by —NR¹CO— or —CONR¹— bonds where R¹ in each case independently denotes hydrogen, methyl or ethyl, and pharmaceutically compatible salts and derivatives thereof.

The monomeric building blocks $X^{21}$ to $X^{30}$ have preferably the following meanings:

$X^{21}$ and $X^{29}$ are α-aminocarboxylic acid building blocks which can be bridged together and they particularly preferably have an SH side chain, in particular a cysteine side chain or a structurally related side chain e.g. a penicillamine side chain. Alternatively $X^{21}$ and $X^{29}$ can also be two α-aminocarboxylic acid residues linked by a thioether group e.g. a lanthionine group.

$X^{22}$ and $X^{27}$ are each independently α-aminocarboxylic acids with an aliphatic side chain, preferably an aliphatic hydrophilic side chain and in particular an amide side chain such as asparagine or glutamine, in particular asparagine.

$X^{23}$ is an α-aminocarboxylic acid with a basic side chain e.g. lysine, ornithine or arginine or with an aliphatic hydrophilic side chain e.g. with an amide side chain such as glutamine or asparagine. $X^{23}$ is particularly preferably lysine.

$X^{24}$ to $X^{25}$ are each independently α-aminocarboxylic acids with an aromatic side chain such as tyrosine, phenylalanine or tryptophan. $X^{24}$ is particularly preferably tyrosine and $X^{25}$ is phenylalanine.

$X^{26}$ is an α-aminocarboxylic acid with an aliphatic side chain, preferably with an aliphatic hydrophilic side chain such as hydroxyvaline, homoserine, serine or threonine, in particular serine. However, $X^{26}$ can also have an aliphatic hydrophobic side chain such as alanine.

$X^{28}$ is an α-aminocarboxylic acid with an aliphatic side chain, preferably with an aliphatic hydrophobic side chain such as valine, norvaline, norleucine, isoleucine, leucine or alanine. $X^{28}$ is particularly preferably isoleucine.

$X^{30}$—if present—is an α-aminocarboxylic acid with an aromatic side chain, preferably with a tryptophan side chain. The tryptophan side chain can be optionally modified for example by reduction.

The peptides according to the invention are preferably derived from the uPA sequence and contain at least 2 and particularly preferably at least 3, for example 4 amino acid residues which also occur at corresponding positions in the native uPA sequence. At least two of the amino acid residues $X^{22}$, $X^{23}$, $X^{24}$, $X^{25}$, $X^{26}$, $X^{28}$ and $X^{30}$ particularly preferably have a side chain which is identical to an amino acid at the same position in the native uPA sequence. Most preferably at least 2 of the amino acid residues $X^{24}$, $X^{25}$, $X^{28}$ and—if present—$X^{30}$ have the same side chain as in the native uPA sequence.

Y is a spacer group e.g. a peptidic spacer group composed of one or several amino acids e.g. poly-Lys or another spacer group e.g. a polyethylene glycol group. The peptide can be coupled to carrier substances via the group Y.

Hence a further subject matter of the present invention are cyclic peptides with a nine-membered ring of which at least two, preferably at least 3 and particularly preferably at least 4 of the amino acids forming the ring have a sequence from the uPA region 22 to 28.

In addition to peptides having the structural formula (I), pharmaceutically compatible salts and derivatives thereof are also suitable as uPA antagonists. Suitable derivatives are in particular compounds in which the reactive groups of the side chain or/and of the N-terminus or C-terminus e.g. amino or carboxylic acid groups have been modified. Examples of such modifications are acylation e.g. an acetylation of amino groups or/and an amidation or esterification of carboxylic acid groups.

Natural amino acids or enantiomers thereof or non-naturally-occurring amino acids such as γ-aminobutyric acid, β-alanine can be used as the aminocarboxylic acids that the building blocks for the peptides according to the invention.

The monomeric building blocks are linked by acid amide bonds $NR^1CO$ or $CONR^1$ i.e. the direction of the peptide sequence can also be reversed (retropeptides). As in native polypeptides, $R^1$ can denote hydrogen. On the other hand, $R^1$ can also denote an alkyl residue e.g. methyl or ethyl and in particular methyl since N-alkylation of the amide bond often has a major influence on the activity (cf. e.g. Levian-Teitelbaum et al., Biopolymers 28 (1989), 51–64).

The α-aminocarboxylic acids can also be used as monomeric building blocks in the form of L-enantiomers or/and D-enantiomers. The spatial structure of the peptides according to the invention can be modified by changing the chirality which can also influence the activity. Retro-inverso peptides are particularly preferred i.e. peptides which are present in a reversed sequence direction and contain D-amino acids as monomeric building blocks. In these retro-inverso structures the functional side chains have a similar spatial orientation to those in the native peptide sequence, but their biological degradation can be impaired due to the presence of D-amino acids and they therefore have advantages as drugs (cf. for example Wermuth et al., J. Am. Chem. Soc. 119 (1997), 1328–1335 and references cited therein).

The peptides according to the invention are preferably cyclic compounds in which in particular the monomeric building blocks $X^{21}$ and $X^{29}$ are bridged together. This bridging can for example utilize the side chains of the respective α-aminocarboxylic acid residues in which case bridging by means of disulfide bonds e.g. between two cysteine residues is particularly preferred. Other types of cyclization between amino acid side chains are, however, also possible e.g. amide bonds between an amino acid with an amino side group e.g. ornithine or Lys and an amino acid with a carboxylic acid side group such as Asp or Glu. In addition the disulfide bridge can also be replaced by an alkylene bridge in order to increase the chemical stability. In addition an amino acid side chain may also be linked to the peptide backbone e.g. an ω-amino side group may be linked to the C-terminal end or a carboxylic acid side group may be linked to the N-terminal end. A linkage of the N-terminus and C-terminus is also possible.

It is particularly preferred when at least one of the amino acids $X^{21}$, $X^{27}$, $X^{29}$ and $X^{30}$ is a D-amino acid. At least one of the amino acids $X^{21}$ to $X^{30}$ is particularly preferably a D-amino acid e.g. D-cysteine.

Instead of the disulfide bridge it is also possible to use so-called turn mimetics (Haubner et al., J. Am. Chem. Soc. 118 (1996), 7884–7891) or sugar amino acids (Graf von R ödern et al., J. Am. Chem. Soc. 118 (1996), 10156–10167).

The peptides according to the invention can be obtained by chemical synthesis as elucidated in the examples. Alternatively the peptides according to the invention can also be components of recombinant polypeptides.

Yet a further subject matter of the present invention are peptides which are derived from the linear peptide uPA (19 to 31) and cyclic derivatives thereof and carry D-amino acid residues at selected positions. Such peptides have the general structural formula (II):

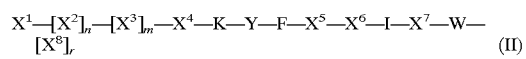
(II)

in which $X^1$ to $X^8$ each denotes an aminocarboxylic acid preferably an α-aminocarboxylic acid and $X^1$ and $X^7$ or $X^1$ and $X^8$ are optionally bridged together, n, m and r are each independently 0 or 1, K is defined as $X^{23}$ and preferably denotes an α-aminocarboxylic acid with a lysine side chain, Y is defined as $X^{24}$ and preferably denotes an α-aminocarboxylic acid with a tyrosine side chain, F is defined as $X^{25}$ and preferably denotes an α-aminocarboxylic acid with a phenylalanine side chain, I is defined as $X^{28}$ and preferably denotes an α-aminocarboxylic acid with an isoleucine side chain, W is defined as $X^{30}$ and preferably denotes an α-aminocarboxylic acid with a tryptophan side chain and the monomeric building blocks are linked by —$CONR^1$— or —$NR^1CO$— bonds where $R^1$ in each case independently denotes hydrogen, methyl or ethyl and pharmaceutically compatible salts and derivatives thereof and in which at least one of the amino acid residues denotes $X^1$, $X^2$, $X^3$, $X^6$, I, $X^7$, W and $X^8$ denotes a D-amino acid residue.

The monomeric building blocks $X^1$ to $X^8$ preferably have the following meanings:

$X^1$ and—if present—$X^8$ correspond to the meaning of $X^{21}$ and $X^{29}$ and are e.g. α-aminocarboxylic acid building blocks with an SH side chain, in particular with a cysteine side chain.

$X^2$—if present—is an α-aminocarboxylic acid with an aliphatic and uncharged side chain e.g. valine, leucine or isoleucine, in particular valine.

$X^3$ and $X^5$ correspond to the meaning of $X^{26}$ and are e.g. α-aminocarboxylic acids with an aliphatic hydrophilic side chain such as serine or threonine, in particular serine.

$X^4$ and $X^6$ correspond to the meaning of $X^{22}$ and $X^{27}$ and are e.g. α-aminocarboxylic acids with an aliphatic hydrophilic side chain, in particular an amide side chain such as asparagine or glutamine, in particular asparagine.

If not bridged with $X^1$, $X^7$ is preferably a basic α-aminocarboxylic acid, in particular histidine. If it is bridged with $X^1$, then $X^7$ is an α-aminocarboxylic acid with an SH side group, in particular cysteine.

The present invention additionally concerns a pharmaceutical composition which contains at least one peptide or polypeptide as defined above as the active substance optionally together with common pharmaceutical carriers, auxiliary agents or diluents. The peptides or polypeptides according to the invention are used especially to produce uPA antagonists which are suitable for treating diseases associated with the expression of uPAR especially for treating tumours.

An additional subject matter of the present invention is the use of peptides derived from the uPA sequence and in particular of uPA antagonists such as the above-mentioned peptides and polypeptides to produce targeting vehicles e.g. liposomes, viral vectors etc. for uPAR-expressing cells. The targeting can be used for diagnostic applications to steer the transport of marker groups e.g. radioactive or non-radioactive marker groups. On the other hand the targeting can be for therapeutic applications e.g. to transport pharmaceutical agents and for example also to transport nucleic acids for gene therapy.

The pharmaceutical compositions according to the invention can be present in any form, for example as tablets, as coated tablets or in the form of solutions or suspensions in aqueous or non-aqueous solvents. The peptides are preferably administered orally or parenterally in a liquid or solid form. When they are administered in a liquid form, water is preferably used as the carrier medium which optionally contains stabilizers, solubilizers or/and buffers that are usually used for injection solutions. Such additives are for example tartrate or borate buffer, ethanol, dimethyl sulfoxide, complexing agents such as EDTA, polymers such as liquid polyethylene oxide etc.

If they are administered in a solid form, then solid carrier substances can be used such as starch, lactose, mannitol, methyl cellulose, talcum, highly dispersed silicon dioxide, high molecular fatty acids such as stearic acid, gelatin, agar, calcium phosphate, magnesium stearate, animal and vegetable fats or solid high molecular polymers such as polyethylene glycols. The formulations can also contain flavourings and sweeteners if desired for oral administration.

The therapeutic compositions according to the invention can also be present in the form of complexes e.g. with cyclodextrins such as γ-cyclodextrin.

The administered dose depends on the age, state of health and weight of the patient, on the type and severity of the disease, on the type of treatment, the frequency of the administration and the type of desired effect. The daily dose of the active compound is usually 0.1 to 50 mg/kilogramme body weight. Normally 0.5 to 40 and preferably 1.0 to 20 mg/kg/day in one or several doses are adequate to achieve the desired effects.

The invention is further illustrated by the examples described in the following and the figures.

EXAMPLES

Figure 1A:
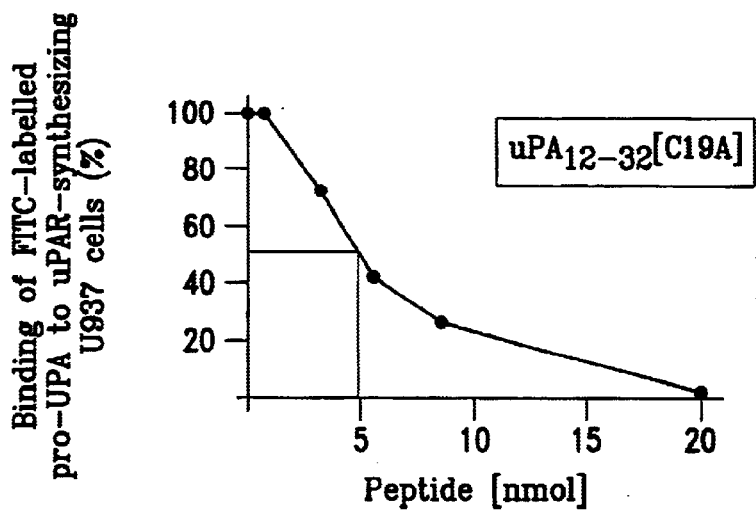
FIG. 1 shows the quantity-dependent inhibition of the binding of pro-uPA to a cell surface-associated uPAR by synthetic peptides.

1. Methods 1.1 Solid Phase Peptide Synthesis

Linear peptides were synthesized on a 2-chlorotrityl resin (Barlos et al., Int. J. Pept. Protein Res. 37 (1991), 513 to 520) using an Applied Biosystems Model 431 A peptide synthesizer or a multiple peptide synthesizer model Syro II (MultiSynTech). Using the orthogonal Fmoc strategy (Carpino and Han, J. Org. Chem. 37 (1972), 3404–3409; Fields and Noble, Int. J. Peptide Protein Res. 35 (1990), 161–214) the amino acid side chains were blocked with the protecting groups trityl (Asn, Cys, Gln and His), tert.-butyloxycarbonyl (Lys and Trp), tert.-butyl (Asp, Glu, Ser, Thr and Tyr), acetamidomethyl (Cys) and 2,2,5,7,8-pentamethylchroman-6-sulfonyl or 2,2,4,6,7-pentamethyldihydrobenzofuran-5-sulfonyl (Arg). The coupling was carried out at room temperature in dimethylformamide using a three-fold excess of 2-(1H-benzotriazol-1-yl)-1,1,3,3-tetramethyl-uroniumtetrafluoroborate/1-hydroxybenzotriazole/Fmoc-amino acid with 2.5 equivalents of N-ethyldiiso-propylamine in N-methyl-pyrrolidone. The Fmoc group was removed by sequential treatment of the resins with an excess of 40% or 20% piperidine in dimethylformamide. The cleavage of the peptides and removal of the side chain protecting groups was carried out simultaneously by treatment with 82.5% trifluoroacetic acid/5% phenol/2.5% ethane dithiol/5% thioanisol/5% $H_2O$ (0° C./1h; room temperature/1h). In the case of Arg groups protected with 2,2,5,5,7,8-pentamethylchroman-6-sulfonyl, the peptides were incubated for an additional 12 h at room temperature. The crude peptides were precipitated at −30° C. with diethyl ether, dissolved in methanol, precipitated as previously described, dissolved in tert.-butanol and lyophilized. Peptides containing tryptophan were additionally treated for 2 h with 5% acetic acid before the lyophilization.

The peptides were purified by HPLC using a reversed phase C18 column (Nucleosil 1005-C18) or a YMC pack ODS column. They were cyclized by forming a disulfide bridge between the cysteine residues. The oxidation required for this was carried out by taking 0.1 to 0.3 mg/ml of the purified linear peptides up in 80% water and 20% DMSO (vol/vol) and removing the solvent under reduced pressure after 10 h. The cyclic peptides were again purified by HPLC as described above.

1.2 Mass Spectroscopy and Amino Acid Analysis

The purified and desalted peptides were analysed on a HPLC system 140 B (Applied Biosystems, Foster City, USA). The UV absorbance was measured with a UVIS 200 detector (Linear Instruments, Reno, USA) at 206 nm. The chromatography was carried out on an Aquapore 3 $\mu$(Applied Biosystems, Foster City, USA) reversed phase column (1 mm×50 mm) at a flow rate of 20 $\mu$l/min. The solvent system was 0.1% TFA in water (A) and 0.1% TFA in acetonitrile (B). The HPLC system was coupled to an atmospheric pressure ionisation source which was connected to a tandem quadrupole instrument API III (Sciex, Perkin Elmer, Thornhill, Canada).

The quadrupole M/Z scale was calibrated with the ammonium addition products of polypropylene glycol. The average mass values were calculated from the M/Z peaks in the charge distribution profiles of the multiple charged ions (Covey et al., Rapid Commun. Mass Spectrom. 2 (1988), 249–256; Fenn et al., Science 246 (1989), 64–71).

The amino acid analysis was carried out according to the ninhydrin method using the analytical system 6300 (Beckman Instruments, Fullerton, USA) after hydrolysing the peptides by the TFA-HCl vapour phase method which allows a quantitative determination of the peptide concentration (Tsugita et al., J. Biochem. 102 (1987), 1593–1597).

1.3 Flow Cytometry

The ability of the synthetic peptides to inhibit the uPA/uPAR interaction was determined by means of flow cytometry on a FACScan flow cytometer (Becton-Dickinson, Heidelberg, Germany) using the human promyeloid cell line U937 as a source of cellular native uPAR (Chuchulowski et al., Fibrinolysis 6, Suppl. 4 (1992), 95–102; Magdolen et al., (1996), supra). The U937 cells were stimulated with 1 mM phorbol-12-myristate-13-acetate (PMA) for 48 h. After stimulation with PMA the U937 cells expressed considerable amounts of cell surface-associated uPAR.

The stimulated cells were treated for 1 min at room temperature with 50 mM glycine HCl, 0.1 NaCl, pH 3.6 in order to dissociate endogenous receptor-bound uPA. Subsequently the acidic buffer was neutralized with 0.5 M HEPES-100 mM NaCl, pH 7.5. The cells were then immediately washed twice with PBS/0.1% bovine serum albumin (BSA) and centrifuged for 10 min at room temperature and 300 x g. The cells were resuspended in PBS/0.1% BSA, adjusted to a concentration of $10^6$ cells per ml and simultaneously incubated for 45 minutes at room temperature with 16 ng FITC-conjugated pro-uPA and various amounts of the synthetic peptides. Before the analysis, propidium iodide, a fluorescent dye which specifically binds double-stranded DNA, was added to each sample in order to determine the viability of the analysed U937 cells. Damaged, propidium iodide-labelled cells were excluded from the analysis.

1.4 Solid Phase uPAR/uPA Binding Test

In addition to the flow cytometric analyses, a solid phase ATF-ligand binding test was carried out in order to examine the interactions of synthetic peptides with the uPAR. For this microtitre plates were coated with recombinant human uPAR from CHO cells (Wilhelm et al., FEBS Lett. 337 (1994), 131–134; Magdolen et al., Electrophoresis 16 (1995), 813–816) and the remaining protein-binding sites were saturated with 2% BSA (weight/vol). After incubation with the samples (0.6 ng ATF together with 15 $\mu$g synthetic peptide per ml) and several wash steps, the amount of ATF which had bound to the uPAR immobilized on the microtitre plate was determined using a biotinylated monoclonal mouse antibody against the kringle domain of ATF (No. 377, American Diagnostics, Greenwich, Conn., USA) and subsequent addition of avidin-peroxidase conjugate and 3,3',5,5'-tetramethylbenzidine/$H_2O$ as a substrate for the peroxidase. The presence of synthetic peptides which compete with the ATF binding to uPAR reduces the conversion of the chromogenic substrate.

2. Results 2.1 Determination of the uPAR Binding Capacity of Synthetic Peptides by Quantitative Flow Cytometric Analysis A comparison was made of the inhibitory capacity of the peptides uPA$_{12-32}$ [C19A] (Appella et al., (1987), supra) the so-called clone 20-peptide AEPMPHSLNFSQYLWYT (SEQ ID NO:1) (Goodson et al., (1994), supra) which was identified as the most effective peptide from a phage peptide library and of the synthetic peptide uPA$_{16-32}$ derived from the wild-type uPA sequence.

Figure 1B:
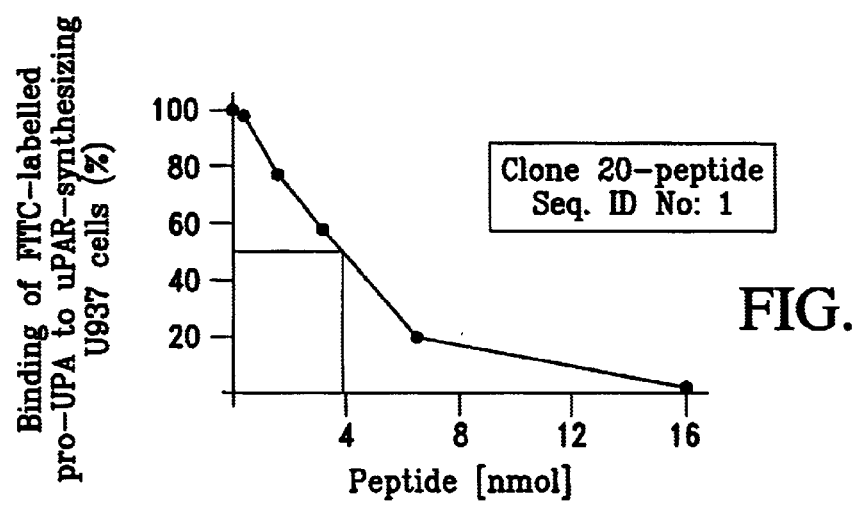
Figure 1C:
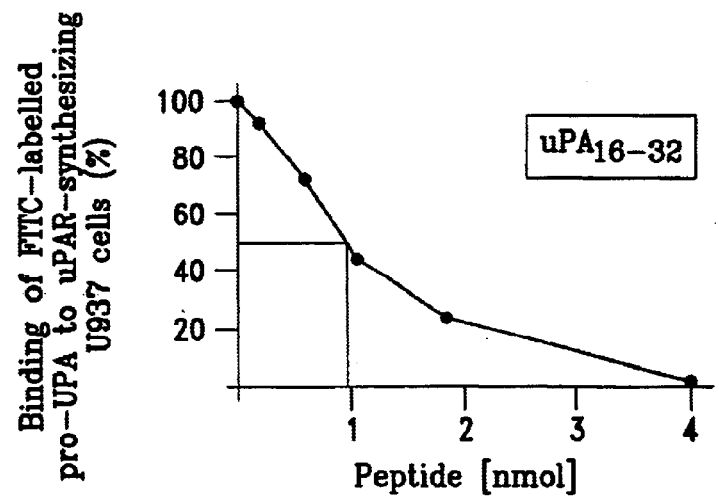

For this the purified peptides were analysed by mass spectroscopy, quantified by amino acid analysis and then tested by flow cytometry according to the method described in 1.3 for their ability to inhibit the binding of fluorescent-labelled pro-uPA to the uPA receptor on U937 cells. It was found that pro-uPA is displaced in a dose-dependent manner from the cell surface-associated uPAR by all three synthetic peptides (FIG. 1). An approximately 15,000 to 12,000 molar excess of uPA$_{12-32}$ [C19A] or clone 20 peptide resulted in a 50% inhibition of the binding of uPA. The peptide uPA$_{16-32}$ exhibited a 4- to 5-fold higher affinity to uPAR compared to the two other peptides: an approximately 3,000-fold molar excess is sufficient to achieve a 50% inhibition.

Furthermore it was found that the linear peptide uPA$_{19-31}$ surprisingly has an IC50 value of ca. 0.8 $\mu$M whereas the IC50 value for uPA$_{16-32}$ is ca. 3.2 $\mu$M.

2.2 Determination of the uPAR Binding Capacity of Synthetic Peptides in a Microtitre Plate Solid Phase Ligand Binding Test A series of peptides with variable sequence regions from the receptor binding region of uPA were synthesized and were increasingly shortened at the amino terminus starting with uPA$_{10-32}$. The microtitre plate solid phase binding test described in 1.4 was used to determine the inhibitory capacity of these peptides. The results of this test are shown in FIG. 2.

Figure 2A:
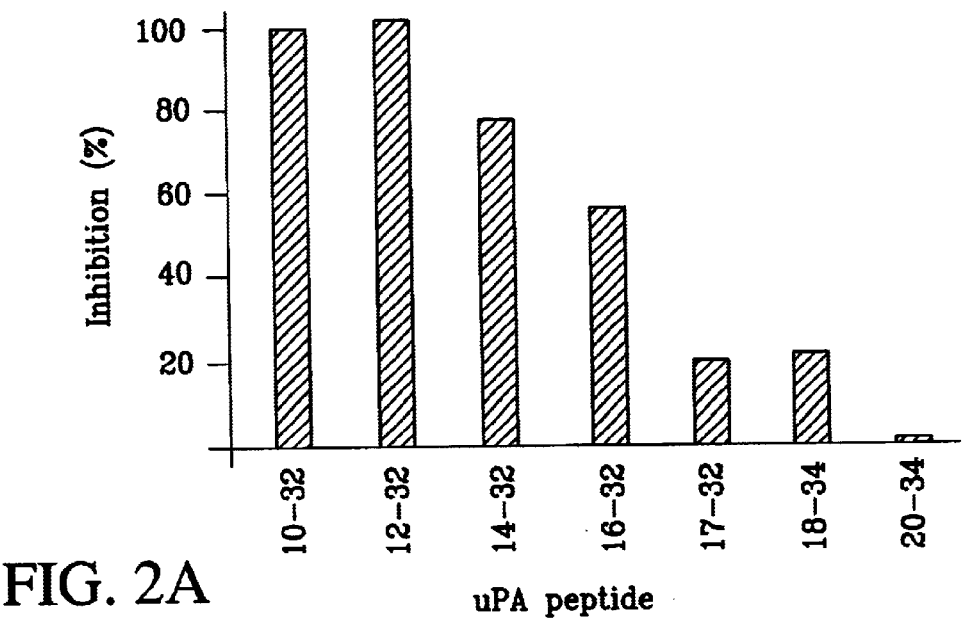
FIG. 2 shows the competition of synthetic peptides with ATF for binding to the uPAR.
Figure 2B:
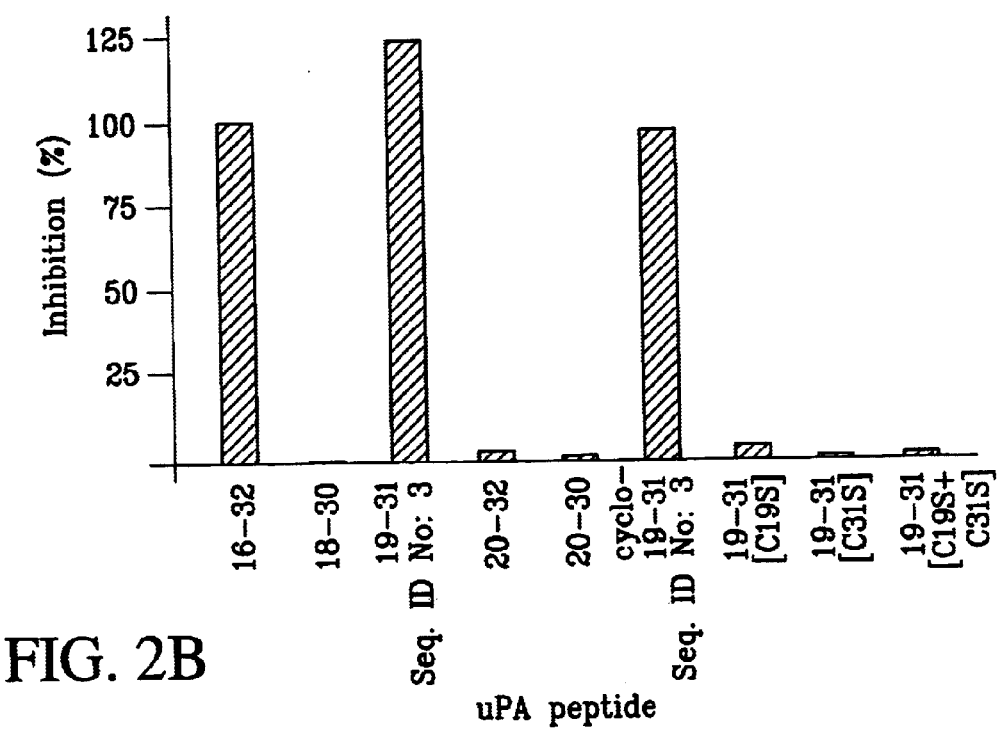

It can be seen in FIG. 2A that the peptides uPA$_{10-32}$, uPA$_{12-31}$, uPA$_{14-32}$ and uPA$_{16-32}$ effectively inhibit the binding of ATF to uPAR. The peptides uPA$_{17-32}$ and uPA$_{18-34}$ have considerably reduced uPAR binding capacities. The peptide uPA$_{20-34}$ does not bind at all to the uPAR. In a further experiment the binding capacity of the peptides uPA$_{19-31}$ (SEQ ID NO: 3), uPA$_{18-30}$, uPA$_{20-32}$ and uPA$_{20-30}$ was tested. The result of this experiment is shown in FIG. 2B. Surprisingly it was found that uPA$_{19-31}$ (SEQ ID NO: 3)

binds to the uPAR with higher affinity than the longer peptide uPA$_{16-32}$. The other tested linear peptides had no significant binding capacity.

The cyclic peptide cyclo$^{19-31}$uPA$_{19-31}$ (SEQ ID NO: 3) which contains an intramolecular disulfide bond between the cysteine residues at positions 19 and 31 was surprising still able to inhibit the binding of uPA to the uPA receptor. Furthermore the binding activity of cyclo$^{19-31}$uPA$_{19-31}$ (SEQ ID NO: 3) was significantly more stable after long storage in aqueous solution or repeated freeze/thaw cycles then that of the linear peptide uPA$_{19-31}$ (SEQ ID NO: 3).

2.3 Systematic replacement of L-amino acids by D-amino acids in chemically synthesized linear and cyclic peptides from the region uPA$_{19-31}$ (SEQ ID NO: 3)

The uPAR binding capacity of synthetic linear and cyclic peptides from the region uPA$_{19-31}$ (SEQ ID NO: 3) was determined by in each case replacing one L-amino acid by the corresponding D-amino acid. The results of this experiment are shown in the following table 1.

| D-amino acid | Peptide structure | Inhibition |
|---|---|---|
| Trp30 | [D-Trp$^{30}$]uPA$_{19-31}$ (SEQ ID NO: 3) | ++ |
| Trp30 | cyclo[D-Trp$^{30}$]uPA$_{19-31}$(SEQ ID NO: 3) | + |
| His29 | [D-His$^{29}$]uPA$_{19-31}$(SEQ ID NO: 3) | ++ |
| His29 | cyclo[D-His$^{29}$]uPA$_{19-31}$(SEQ ID NO: 3) | + |
| Asn27 | [D-Asn$^{27}$]uPA$_{19-31}$(SEQ ID NO: 3) | ++ |
| Asn27 | cyclo[D-Asn$^{27}$]uPA$_{19-31}$(SEQ ID NO: 3) | ++ |
| Ser21 | [D-Ser$^{21}$]uPA$_{19-31}$(SEQ ID NO: 3) | ++ |
| Ser21 | cyclo[D-Ser$^{21}$]uPA$_{19-31}$(SEQ ID NO: 3) | ++ |
| Val20 | [D-Val$^{20}$]uPA$_{19-31}$(SEQ ID NO: 3) | ++ |
| Val20 | cyclo[D-Val$^{20}$]uPA$_{19-31}$(SEQ ID NO: 3) | + |
| Cys19 | [D-Cys$^{19}$]uPA$_{19-31}$(SEQ ID NO: 3) | +++ |
| Cys19 | cyclo[D-Cys$^{19}$]uPA$_{19-31}$(SEQ ID NO: 3) | +++ |
| cyclo19–31 | cyclo[19–31]uPA$_{19-31}$(SEQ ID NO: 3) | +++ |

It can be seen from this table that the introduction of D-amino acids at positions Cys19, Val20, Ser21, Asn27, His29 and Trp30 in the linear as well as in the cyclic peptides is possible without loss of the inhibitory effect. Moreover it was found that in the case of the linear peptides the inhibitory effect is not lost by introducing D-amino acids at positions Ile28 and Cys31.

2.4 Synthesis of Modified Cyclic uPA Peptides

Figure 3A:
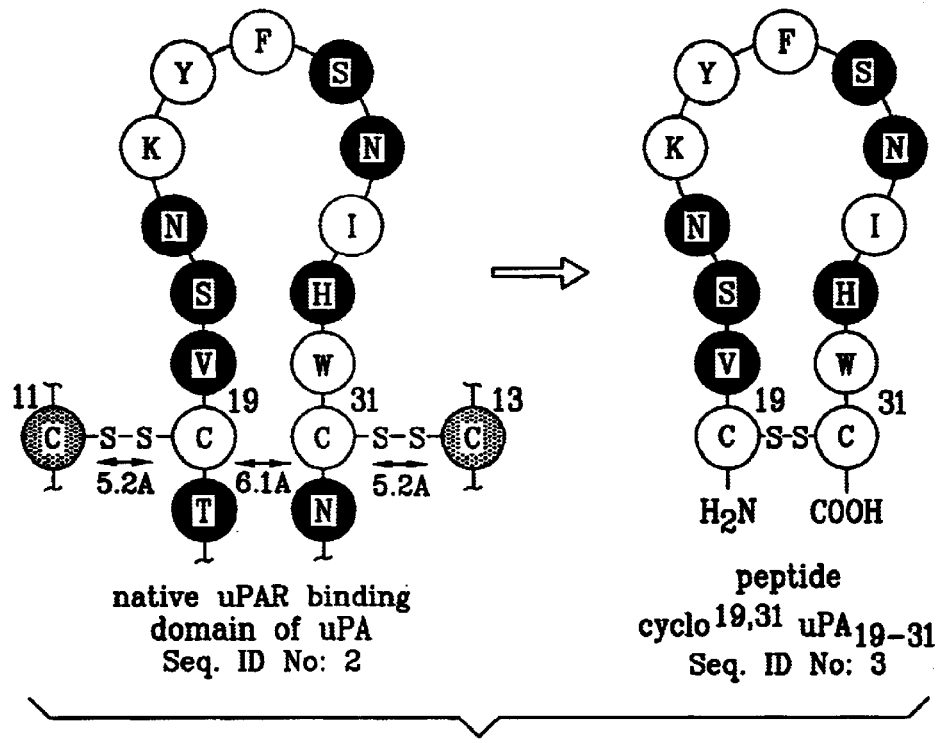
FIG. 3A shows the structure of $cyclo^{19-31}$ uPA 19–31 (right) (SEQ ID NO: 3) compared to the structure of the corresponding domain from native uPA (SEQ ID NO: 2)
Figure 3B:
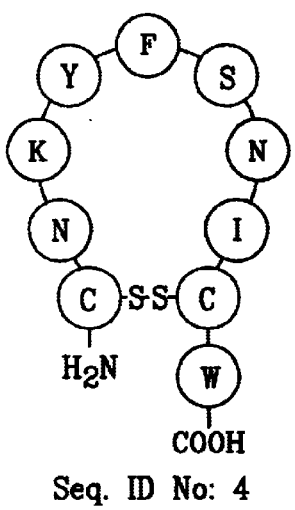
FIG. 3B shows the structure of the cyclic peptide derivative $cyclo^{21,29}$ [Cys21,29] $uPA_{21-30}$ (SEQ ID NO: 4).

Using cyclo19,31uPA$_{19-31}$ (SEQ ID NO: 3) as the lead structure, a cyclic peptide was prepared in which certain amino acids were deleted and/or substituted by other amino acids. The structure of this new synthetic peptide variant cyclo$^{21,29}$[Cys21,29]uPA$_{21-30}$ (SEQ ID NO: 4) is shown in FIG. 3. In contrast to the synthetic method stated in 1.1 this peptide was prepared on a trityl chloride polystyrene resin.

Figure 4:
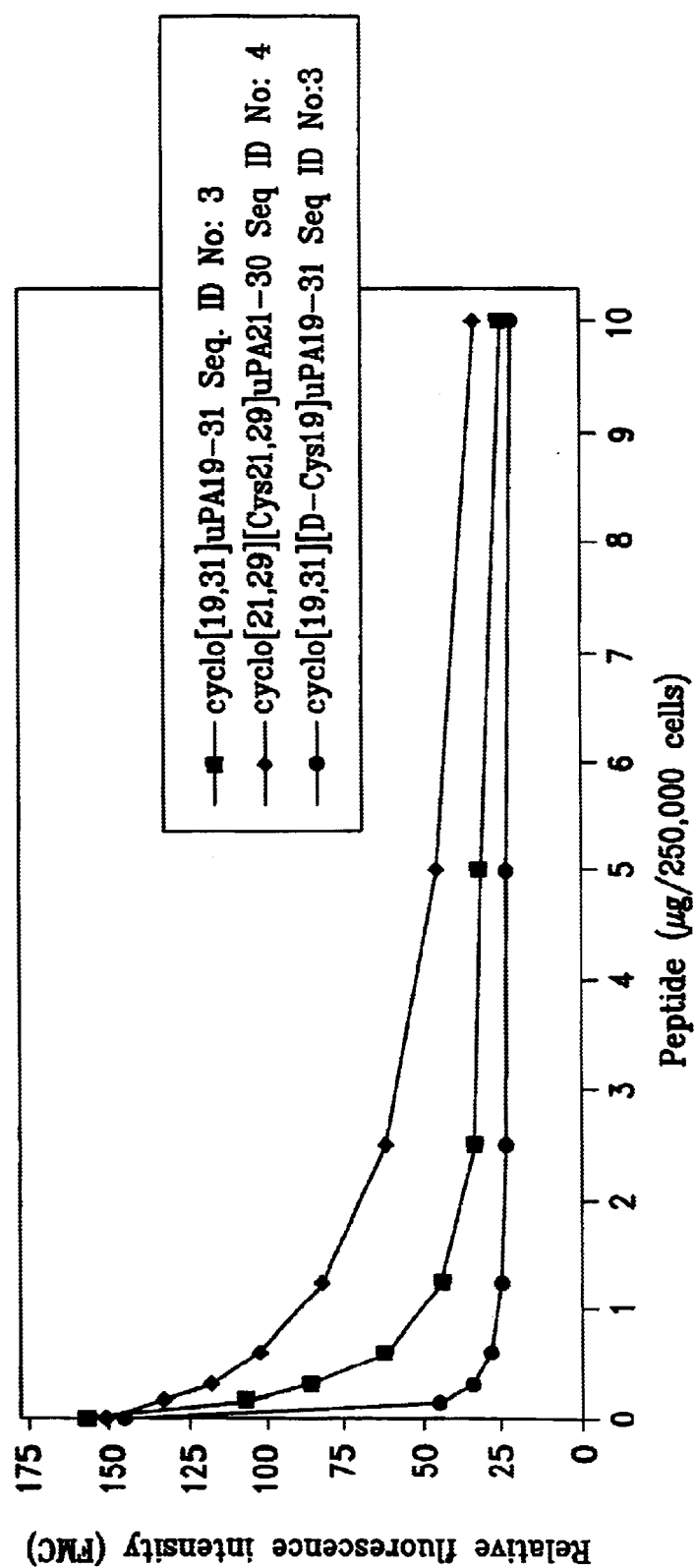
FIG. 4 shows the inhibition of the uPA/uPAR interaction by synthetic peptides and FIG. 5 shows the inhibition of tumour growth in naked mice by administration of synthetic peptides.

FIG. 4 shows the inhibitory effect of this synthetic peptide variant compared to cyclo$^{19,31}$uPA$_{19-31}$ (SEQ ID NO: 3) and cyclo$^{19,31}$[D-Cys19]uPA$_{19-31}$ (SEQ ID NO: 3).

2.5 In vivo Effect $6 \times 10^6$ human breast cancer cells MDA-MB-231 (Price et al., Cancer Res. 50 (1990), 717–721) in a total volume of 300 µl were injected into the right side of 4–6 week old Balbc/3 naked mice. Before injection the cancer cells were mixed with 200 µg of the cyclic uPA peptides cyclo$^{19,31}$uPA$_{19-31}$ (SEQ ID NO: 3) and Cyclo$^{21,29}$[Cys21,29]uPA$_{21-30}$ (SEQ ID NO: 4) in PBS, pH 7.4. Subsequently the mice were treated twice weekly intraperitoneally with the respective peptide at a dose of 10 mg/kg body weight (injection volume 300 µl). The volume of the primary tumours which occurred in the mice in cm$^3$ was determined after 1, 2, 3 and 5 weeks by measuring the two largest diameters. The control mice were administered PBS pH 7.4. Each group was composed of 5 mice. The results for the peptide cyclo$^{19,31}$uPA$_{19-31}$ (SEQ ID NO: 3) are shown in Tab. 2.

TABLE 2

| Week | Control | uPA peptide |
|---|---|---|
| 1 | 0 | 0 |
| 2 | 0.34 ± 0.3 | 0.086 ± 0.047 |
| 3 | 0.71 ± 0.5 | 0.303 ± 0.129 |
| 5 | 2.33 ± 0.32 | 0.62 ± 0.21* |

*p = 0.02

Figure 5:
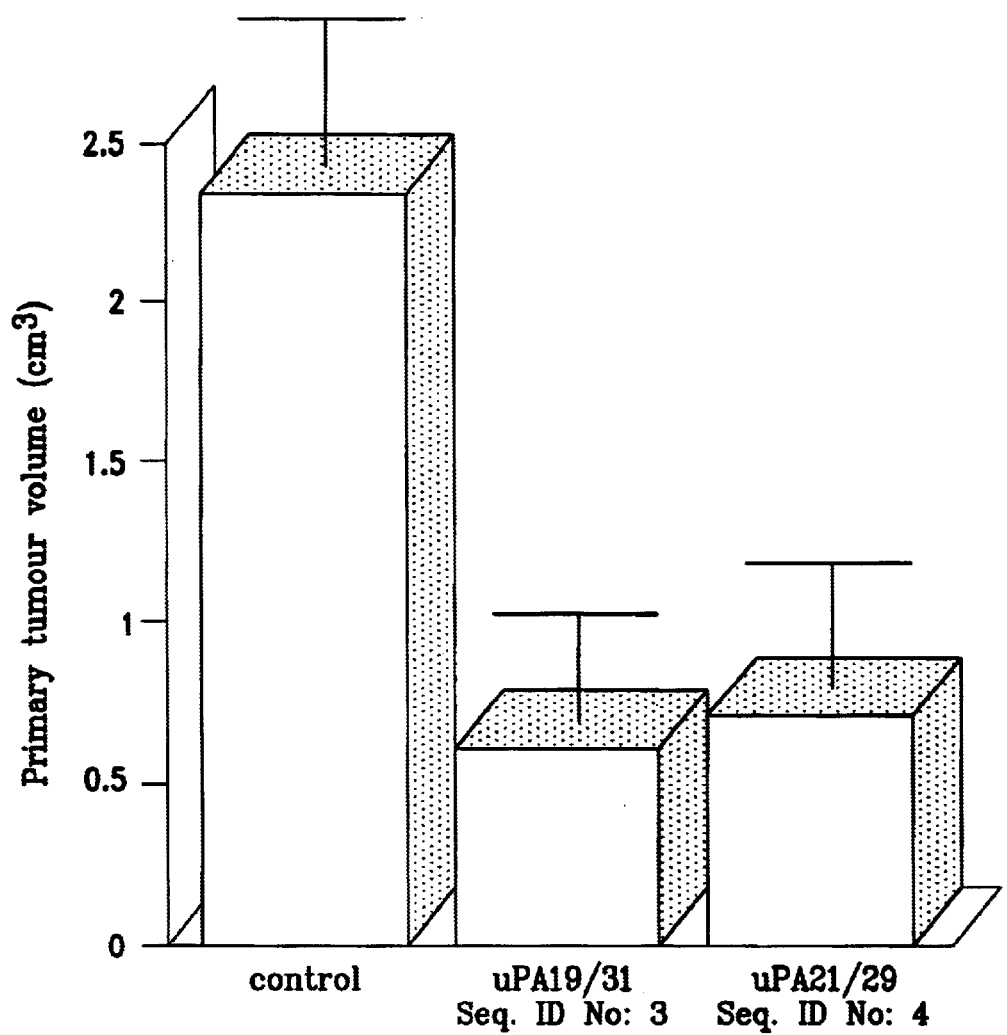

The volume of the primary tumour after a five week treatment is shown in FIG. 5. It can be seen that the administration of both peptides led to a significant reduction of the tumour growth in vivo.

What is claimed is:

1. A peptide comprising monomeric building blocks and having the general structural formula (I):

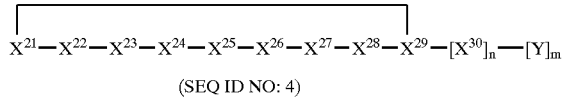

(SEQ ID NO: 4)

in which $X^{21}$ to $X^{30}$ each denotes an aminocarboxylic acid and $X^{21}$ and $X^{29}$ are bridged together, Y is a spacer group that can couple the peptide to carrier substances n and m are each independently 0 or 1, and the monomeric building blocks are linked by —$NR^1CO$— or —$CONR^1$— bonds where $R^1$ in each case independently denotes hydrogen, methyl or ethyl, and wherein the amino acid residues $X^{21}$–$X^{30}$ each independently have one of the following meanings:

(i) $X^{21}$ and $X^{29}$ are each independently an aminocarboxylic acid residue with an SH side chain or $X^{21}$ and $X^{29}$ are together two aminocarboxylic acid residues which are bridged by a thioether bond;

(ii) $X^{22}$ and $X^{27}$ are each independently an aminocarboxylic acid residue with an aliphatic side chain;

(iii) $X^{23}$ is an aminocarboxylic acid residue with a basic or an aliphatic hydrophilic side chain;

(iv) $X^{24}$, $X^{25}$ and $X^{30}$ are each independently an aminocarboxylic acid residue with an aromatic side chain, (v) $X^{26}$ is an aminocarboxylic acid residue with an aliphatic side chain, and (vi) $X^{28}$ is an aminocarboxylic acid residue with an aliphatic side chain;

and a pharmaceutically compatible salt or derivative thereof.

2. A peptide as claimed in claim 1,
wherein
(i) $X^{24}$ has a tyrosine side chain;
(ii) $X^{25}$ has a phenylalanine side chain;
(iii) $X^{28}$ has an alanine, leucine or isoleucine side chain, and
(iv) $X^{30}$ has an optionally modified tryptophan side chain.

3. A peptide as claimed in claim 1,
wherein
at least 2 of the amino acid residues $X^{22}$, $X^{23}$, $X^{24}$, $X^{25}$, $X^{26}$, $X^{27}$, $X^{28}$ and $X^{30}$ have an identical side chain to an amino acid at the corresponding $X^{22}$, $X^{23}$, $X^{24}$, $X^{25}$, $X^{26}$, $X^{27}$, $X^{28}$ and $X^{30}$ position in a native uPA sequence.

4. A peptide as claimed in claim 3,
wherein
at least 2 of the amino acid residues $X^{24}$, $X^{25}$, $X^{28}$ and $X^{30}$ have the same side chain as an amino acid at the corresponding $X^{24}$, $X^{25}$, $X^{28}$ and $X^{30}$ position in the native uPA sequence.

5. A peptide as claimed in claim 1, wherein $X^{21}$ and $X^{29}$ are bridged via side chains of amino-carboxylic acid residues.

6. A peptide as claimed in claim 5, wherein $X^{21}$ and $X^{29}$ are bridged by means of disulfide bonds.

7. Pharmaceutical composition suitable for inhibiting the binding of urokinase to a urokinase receptor comprising at least one peptide or polypeptide as claimed in claim 1 as an active substance and at least one pharmaceutically acceptable carrier, auxiliary agent or diluent.

8. The peptide of claim 1, wherein the side chains of $X^{22}$ and $X^{27}$ are aliphatic hydrophilic side chains.

9. The peptide of claim 1, wherein the side chains of $X^{22}$ and $X^{27}$ are amide side chains.

10. The peptide of claim 1, wherein the side chain of $X^{26}$ is an aliphatic hydrophilic side chain.

11. The peptide of claim 1, wherein the side chain of $X^{26}$ is a hydroxy side chain.

12. The peptide of claim 1, wherein the side chain of $X^{28}$ is an aliphatic hydrophobic side chain.

13. The peptide of claim 2, wherein the side chain of $X^{28}$ an isoleucine side chain.

14. A polypeptide comprising at least two peptides wherein at least one of said peptides comprises monomeric building blocks and has the general structural formula (I):

(I)

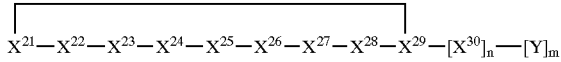

(SEQ ID NO: 4)

in which $X^{21}$ to $X^{30}$ each denotes an aminocarboxylic acid and $X^{21}$ and $X^{29}$ are bridged together, Y is a spacer group that can couple the peptide to carrier substances n and m are each independently 0 or 1, and the monomeric building blocks are linked by —$NR^1CO$— or —$CONR^1$— bonds where $R^1$ in each case independently denotes hydrogen, methyl or ethyl, and wherein the amino acid residues $X^{21}$–$X^{30}$ each independently have one of the following meanings:

(i) $X^{21}$ and $X^{29}$ are each aminocarboxylic acid residues with an SH side chain or 2 aminocarboxylic acid residues which are bridged by a thioether bond;

(ii) $X^{22}$ and $X^{27}$ are each independently aminocarboxylic acid residues with an aliphatic side chain;

(iii) $X^{23}$ is an aminocarboxylic acid residue with a basic or an aliphatic hydrophilic side chain;

(iv) $X^{24}$, $X^{25}$ and $X^{30}$ are each independently aminocarboxylic acid residues with an aromatic side chain, (v) $X^{26}$ is an aminocarboxylic acid residue with an aliphatic side chain, and (vi) $X^{28}$ is an aminocarboxylic acid residue with an aliphatic side chain;

or a pharmaceutically compatible salt and derivative thereof.

15. A polypeptide as claimed in claim 14, wherein (i) $X^{24}$ has a tyrosine side chain;

(ii) $X^{25}$ has a phenylalanine side chain;

(iii) $X^{28}$ has an alanine, leucine or isoleucine side chain, and (iv) $X^{30}$ has an optionally modified tryptophan side chain.

16. A polypeptide as claimed in claim 14, wherein at least 2 of the amino acid residues $X^{22}$, $X^{23}$, $X^{24}$, $X^{25}$, $X^{26}$, $X^{27}$, $X^{28}$ and $X^{30}$ identical side chain to an amino acid at the corresponding $X^{22}$, $X^{23}$, $X^{24}$, $X^{25}$, $X^{26}$, $X^{27}$, $X^{28}$ and $X^{30}$ position in a native uPA sequence.

17. A polypeptide as claimed in claim 14, wherein at least 2 of the amino acid residues $X^{24}$, $X^{25}$, $X^{28}$ and $X^{30}$ have the same side chain as an amino acid at the corresponding $X^{24}$, $X^{25}$, $X^{28}$ and $X^{30}$ position in the native uPA sequence.

18. A polypeptide as claimed in claim 14, wherein X21 and X29 are bridged via side chains of amino-carboxylic acid residues.

19. A polypeptide as claimed in claim 18, wherein $X^{21}$ and $X^{29}$ are bridged by means of disulfide bonds.

20. The polypeptide of claim 14, wherein the side chains of $X^{22}$ and $X^{27}$ are aliphatic hydrophilic side chains.

21. The polypeptide of claim 14, wherein the side chains of $X^{22}$ and $X^{27}$ are amide side chains.

22. The polypeptide of claim 14, wherein the side chain of $X^{26}$ is an aliphatic hydrophilic side chain.

23. The polypeptide of claim 14, wherein the side chain of $X^{26}$ is a hydroxy side chain.

24. The polypeptide of claim 14, wherein the side chain of $X^{28}$ is an aliphatic hydrophobic side chain.

25. The polypeptide of claim 14, wherein the side chain of $X^{28}$ an isoleucine side chain.

26. A polypeptide comprising monomeric building blocks and having the general structural formula (I):

(I)

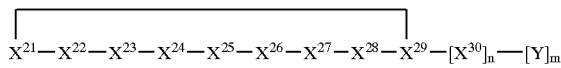

(SEQ ID NO: 4)

in which $X^{21}$ to $X^{30}$ each denotes an aminocarboxylic acid and $X^{21}$ and $X^{29}$ are bridged together, $X^{22}$ and $X^{27}$ are each independently aminocarboxylic acid residues with a side chain comprising at least one amino acid independently selected from the group consisting of asparagine and glutamine;

$X^{23}$ is an aminocarboxylic acid residue with a basic or a hydrophilic side chain comprising at least one amino acid independently selected from the group consisting of asparagine and glutamine;

$X^{26}$ is an aminocarboxylic acid residue with a side chain comprising at least one amino acid independently selected from the group consisting of hydroxyvaline, homoserine, serine, threonine, and alanine, $X^{28}$ is an aminocarboxylic acid residue with a side chain comprising at least one amino acid independently selected from the group consisting of valine, norvaline, norleucine, isoleucine, leucine, or alanine, $X^{29}$ is an aminocarboxylic acid residue with an aliphatic side chain, Y is a spacer group that can couple the peptide to carrier substances n and m are each independently 0 or 1, and the monomeric building blocks are linked by —$NR^1CO$— or —$CONR^1$— bonds where $R^1$ in each case independently denotes hydrogen, methyl or ethyl, and a pharmaceutically compatible salt or derivative thereof.

* * * * *

UNITED STATES PATENT AND TRADEMARK OFFICE
CERTIFICATE OF CORRECTION

PATENT NO. : 6,872,702 B1
DATED : March 29, 2005
INVENTOR(S) : Horst Kessler

It is certified that error appears in the above-identified patent and that said Letters Patent is hereby corrected as shown below:

Title page,
Item [22], PCT Filed, should read -- Apr. 14, 1998 --

Signed and Sealed this

Twenty-sixth Day of July, 2005

JON W. DUDAS
*Director of the United States Patent and Trademark Office*